United States Patent [19]
Howland et al.

[11] Patent Number: 4,834,528
[45] Date of Patent: May 30, 1989

[54] INFRARED PHOTORETINOSCOPE

[75] Inventors: Howard C. Howland; Frank Schaeffel; Leslie Farkas, all of Ithaca, N.Y.

[73] Assignee: Cornell Research Foundation, Inc., Ithaca, N.Y.

[21] Appl. No.: 896,705

[22] Filed: Aug. 15, 1986

[51] Int. Cl.$^4$ .......................... A61B 3/10; A61B 3/14
[52] U.S. Cl. .................................... 351/211; 351/206
[58] Field of Search ................ 351/206, 221, 211, 234

[56] References Cited
U.S. PATENT DOCUMENTS

| 1,631,329 | 6/1927 | Patterson . | |
|---|---|---|---|
| 2,331,591 | 10/1943 | Arnesen . | |
| 2,501,438 | 3/1950 | Copeland . | |
| 2,715,352 | 8/1955 | Jobe . | |
| 3,136,839 | 6/1964 | Sofir | 351/211 |
| 3,639,041 | 2/1972 | Cornsweet . | |
| 3,879,113 | 4/1975 | Howland et al. . | |
| 4,432,617 | 2/1984 | Itoh et al. . | |

OTHER PUBLICATIONS

Howland, "Optics of Photoretinoscopy: Results from Ray Tracing", *American Journal of Optometry & Physiological Optics*, vol. 62, pp. 621–625, Sep., 1985.
Howland et al., "Photorefraction: A Technique for Study of Refractive State at a Distance", *Journal of the Optical Society of America*, vol. 64, No. 2, pp. 240–249, Feb., 1974.
Howland et al., "Optics of Photorefraction: Orthogonal and Isotropic Methods", *Journal of the Optical Society of America*, vol. 73, pp. 1701–1708, Dec., 1983.

*Primary Examiner*—Bruce Y. Arnold
*Assistant Examiner*—Jay Ryan
*Attorney, Agent, or Firm*—Jones, Tullar & Cooper

[57] ABSTRACT

A retinoscope utilizing a plurality of infrared light sources each positioned at a difference distance, or eccentricity, from the optical axis of a camera is disclosed. The plural light sources are scanned while the fundus reflex is observed. Whether or not a reflex can be detected depends on the defocus of the eye relative to the camera, the pupil size, the eccentricity of the light source from the optical axis, and the camera-to-subject distance. The light sources are preferably light emitting diodes which are flashed repeatedly and sequentially. One-half of the camera aperture is occluded to permit determination of the amount and the direction of defocus. By noting which LED just creates a crescent of light in the pupil, and by measuring the pupil diameter, the relative defocus of the eye is determined.

29 Claims, 2 Drawing Sheets

INFRARED PHOTORETINOSCOPE

BACKGROUND OF THE INVENTION

This invention was made with Government support under Grant No. NIH-ROI-EY-02944, awarded by the Department of Health and Human Services, National Institute of Health, National Eye Institute. The Government has certain rights in the invention.

The present invention relates, in general, to the fields of ophthalmology and optometry, and more particularly relates to an improved apparatus and method for measuring the plane of focus of the eye with little or no cooperation from the subject.

The problem of evaluating the optical characteristics of the eye of a subject, such as a small child, who is unable to cooperate with the testing procedure is a substantial one, and a great deal of attention has been placed on the development of objective methods and apparatus for this purpose, an objective method being one wherein the subject's appraisal of the test results is not essential to the measurement. One of the most commonly used devices for providing such measurements is the retinoscope, which generates a light beam in such a manner as to permit the observer to look along the beam axis toward whatever is illuminated. The beam of light is directed toward the subject's pupil so that the observer can view the pupil through an aperture and watch for a "reflex" action in the eye. A typical retinoscope is shown and described in U.S. Pat. No. 2,715,352.

The reflex action which is viewed through a retinoscope appears as an illumination of the pupil, the pupil being alternately illuminated and darkened as the beam of light is swept across the pupil. This is not a direct illumination of the pupil by the incident light beam, but rather is a reflection of light from the subject's retina back through the pupil to the observer. The characteristics of this reflex action enable the operator to determine the location of the plane of focus of the eye and thus to determine whether the subject's eye is normal or is ametropic; i.e., is nearsighted (myopic) or is farsighted (hyperopic), and further to determine the degree of such wear or farsightedness; i.e., to evaluate the degree of defocus of the eye.

Although retinoscopes are widely used, difficulties are encountered, since it is a hand-manipulated device and proper use is thus dependent on the operator's skill, not only in properly illuminating the subject's retina, but in evaluating the resultant reflex. Accordingly, retinoscopy is not really objective, because subjective appraisal of the reflex is necessary. Furthermore, the brightness of the light tends to change the size of the subject's pupil during the examination, and, in addition, only one eye at a time can be examined, so that it is difficult to detect differences in the amount of defocus.

Numerous devices and techniques have been developed over the years to improve on the basic retinoscope and to provide a greater amount of objectivity in the measurement. One such device is described in U.S. Pat. No. 3,136,839, which provides a device for automatically measuring the refractive properties of the eye as well as inanimate lens systems. The device includes a mechanism for periodically scanning the subject lens with radiant energy, detecting the resultant reflex with photosensitive apparatus, and evaluating the detected reflex. Movement of the light source is accomplished by a variety of methods and the entire pupil of the subject's eye is illuminated by the source. If the observer is located at the focal plane of the eye, the observer will see a reflex image of alternate illumination and darkness of the entire pupil as the light source is moved. However, when the observer is not at the focal plane of the eye, motion of the light source will cause the reflex illumination to sweep across the retina, producing partial but increasing illumination of the pupil until total illumination is observed, and thereafter declining illumination toward total darkness. This variation in the reflex is detected in U.S. Pat. No. 3,136,839, by means of suitable photosensitive cells which produce outputs that vary in accordance with the scanning of the pupil by an incident light beam. The insertion of selected lenses between the eye and the photocell will move the effective position of the observer with respect to the focal plane of the eye and will therefore change the time relationship of the cell outputs from the photosensitive detector. The time relationship of the photocell outputs can then be evaluated to detect differences in the time of occurrence of the cell outputs and provide an output related to the lead-lag time relationship between these responses, thereby permitting evaluation of the refractive condition of the eye.

SUMMARY OF THE INVENTION

It is an object of the present invention to provide apparatus for measuring the plane of focus of an eye with improved sensitivity and accuracy and with improved objectivity.

It is a further object of the present invention to provide apparatus for evaluating the optical characteristics of an eye without the need for complex and expensive equipment, and without the need for multiple steps in the measurement which require the patient to undergo testing for an extended period of time.

It is another object of the invention to provide apparatus for measuring the degree of defocus of both eyes of a patient at the same time in order not only to determine the characteristics of the eyes, but also to determine with a high degree of accuracy any differences between the reflex response of the two eyes.

It is a further object of the invention to provide a device for evaluating the degree of defocus of a subject's eyes along any meridian, and to make such measurements rapidly and accurately without the need for cooperation from the subject.

The present invention takes advantage of the fact that when a point source of light is directed into a subject's eye, the light will strike the retina in a point for a normal eye, but for ametropic eyes; that is, eyes that are not properly focused, the point source will appear as a blur spot on the retina. The reflex action of the retina will reproduce an image of the spot at a location near the source, where the reflex image may be viewed or otherwise detected. In the case of a normally focused eye, the reflex image will be essentially the same size as the point source, while for ametropic eyes, the reflex image will be a defocused image of the blur spot, called the "point spread". The image so obtained is a function of the degree of defocus of the eye, the distance of the source and of the detector from the eye, the radius of the subject's pupil, and the distance between the point source of light and the edge of the detector. This distance between the source and the edge of the detector may be referred to as the eccentricity of the source.

By determining the size of the point spread, the degree of defocus can be ascertained. This is accomplished, in accordance with the present invention, by the provision of a video camera as a detector, with the camera lens registering the reflex image. The bottom half of the camera lens is occluded by an opaque shield on which, or in front of which is mounted a plurality of light sources. The light sources are preferably arranged in a row along a radius of the lens extending from its optical axis, and in the simplest form of the invention, this row of light sources is aligned vertically, extending downwardly from the axis. The plural light sources are preferably light emitting diodes which are connected to a suitable source of pulses which successively illuminate the LED's in sequence to produce brief flashes of light. In a preferred form of the invention, the LED's produce light in the infrared range rather than in the visible range in order to reduce the apparent intensity of the light source. This allows the pupil of the subject to remain wide open, if the testing is done in a dimly lit room, thereby increasing the sensitivity of the instrument.

In a further embodiment of the invention, additional rows of light sources may be provided to permit measurement of the reflex action in the eyes of the patient along different axes, or meridians, so as to measure astigmatism. In one form, the plural rows of lights may be provided on an annular shield, with the eccentricity of each light source being determined by its distance from the central aperture. The rows of light sources are placed along selected radii spaced around the shield, and the lights are illuminated sequentially, in one row at a time to permit measurement of the reflex action of the eyes along a plurality of axes in sequence to measure the optical characteristics of the eye.

In accordance with the present invention, the images registered by the camera lens are directed to a suitable infrared sensitive video image tube which transfers the images detected by the camera lens onto a television screen for viewing and evaluation by the operator. Also, the images may be recorded, as on a video cassette recorder, for later evaluation.

As noted above, if the subject's eye is defocused, the reflex action of the eye will produce a blur image at the camera lens adjacent the light source, with the size of the blur image being dependent on the degree of defocus. Accordingly, a given eye having a specific degree of defocus will produce a blur image of a determinable size at the camera lens. The closer the light source is to the edge of the camera aperture, the more of the blur image that will appear in the camera lens, and thus the fuller the reflex image will be. As the source of light moves away from the aperture, the portion of the reflex image which falls on the aperture is reduced to a smaller and smaller crescent, until eventually the reflex image disappears from the aperture. By determining which light source is illuminated when the smallest crescent of light appears in the camera aperture, the degree of eccentricity of the point light source from the edge of the aperture can be determined, and from this the plane of focus of the eye can also be determined. This can be done for a plurality of meridians to determine not only defocus but astigmatism and since both eyes are done at once, the measurements can be made for both eyes and determinations made as to their differences. Accordingly, a simple, yet accurate photoretinoscope is provided which provides highly objective yet very accurate measurements of the optical characteristics of the eye of a subject.

DESCRIPTION OF PREFERRED EMBODIMENTS

The foregoing, and additional objects, features and advantages of the present invention will become apparent from a consideration of the following detailed description of preferred embodiments thereof, taken with the accompanying drawings, in which.

DESCRIPTION OF PREFERRED EMBODIMENTS

Figure 1:
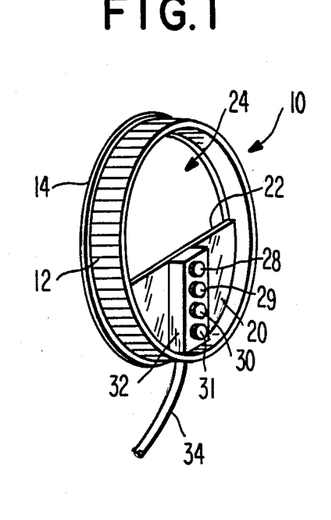
FIG. 1 is a perspective view of an infrared photoretinoscope constructed in accordance with the present invention.

Turning now to a more detailed consideration of the present invention, there is generally indicated at 10 in FIG. 1 an infrared photoretinsocope having a housing which consists of a support ring 12 including threads 14 for attachment to the lens tube 16 (FIG. 2) of a camera such as a video camera generally indicated at 18. The ring 12 carries an opaque light shield 20 to block the passage of light through a selected part of the ring, the shield being substantially semicircular in the illustrated embodiment. The light shield has a top edge 22 which forms a chord across the ring, and defines the edge of a light aperture 24, through which light can pass to the lens 26 in lens tube 16 and then to the video camera 18. Mounted on the front of the light shield 20 are a plurality of light sources 28–31 which may be four light emitting diodes (LED's ) or may be the tips of fiber optic light guides which transfer the light to points 28–31 from remote lamps of suitable intensity and color. The light sources preferably are mounted in a suitable housing 32, although they may be mounted directly on the shield 20, if desired.

The light sources are connected through a suitable electrical cable 34 to a light scanner 36 which may be in the form of electronic circuitry for activating the LED devices 28–31. Alternatively, the cable may consist of a bundle of fiber optic light guides leading to corresponding lamps located in the scanner 36, which then flashes the lamps repeatedly and sequentially to produce bursts of light from sources 28–31. In either form, the scanner operates to illuminate the light sources sequentially at a rate of from 1–10 Hz, preferably. If desired, the frequency of the flashing cycle can be continuously varied between selected limits.

The light sources 28–31 are aligned along a radius of the ring 12 and face in a direction parallel to the optical axis of the camera. In the form of the invention illustrated in FIG. 1, the radial line on which the sources lie is perpendicular to the edge 22 of shield 20. Preferably, edge 22 lies slightly above the axis of ring 12 so that the shield is slightly larger than one-half the area of the ring, while the uppermost light source 28 lies slightly below the ede 22 and below the axis 38 of the ring. The distance between the edge 22 and the center point of the light source 28 is indicated by the arrows 40 in FIG. 2 and is defined as the eccentricity of the light source. As will be seen from FIGS. 1 and 2, the eccentricity is different for each of the light sources 28-31.

When the ring 12 of the photoretinoscope is mounted on the camera 18, the axis 38 of the ring coincides with the axis of the camera and becomes the optical axis of the system when the camera is aligned with and focused on the eye 50 of a subject. When the retinoscope is so arranged, the light sources are illuminated sequentially to provide a scan of the retina 52 in the eye. Although four light sources are illustrated herein, it will be apparent that additional lights may be provided if desired, to provide a greater number of increments in the motion of the light across the retina. As the different lights are illuminated, the reflex image from the retina in the subject's pupil is monitored by the video camera and may be displayed on a suitable video display screen 54. In addition, or alternatively, the reflex image may be recorded on a suitable video recorder 56. Whether or not a reflex can be detected from a given light source depends upon the defocus of the eye with respect to the camera lens, as well as on the pupil size and the distance between the camera and the subject. Thus, as the images from each light source are recorded, the source of light in operation at that instant is also recorded so that the eccentricity of the light source producing a particular image will be known.

As the LED's are flashed, the motion of the reflex image can be seen on the display 54, in those cases where the eye is not focused, and the amount of defocus estimated. If the eye is focused in the camera plane, no motion will be seen. By noting which light source creates the smallest crescent of light in the pupil, and by measuring the pupil diameter, the relative defocus of the eye can be roughly determined from the display.

A more accurate determination of defocus can be obtained by measuring the dark fraction (DF) of the eye. This dark fraction is the ratio of the portion of the diameter of the pupil which is dark to the portion of the diameter which is illuminated by the reflex from the retina (i.e. the fundus reflex).

Figure 2:
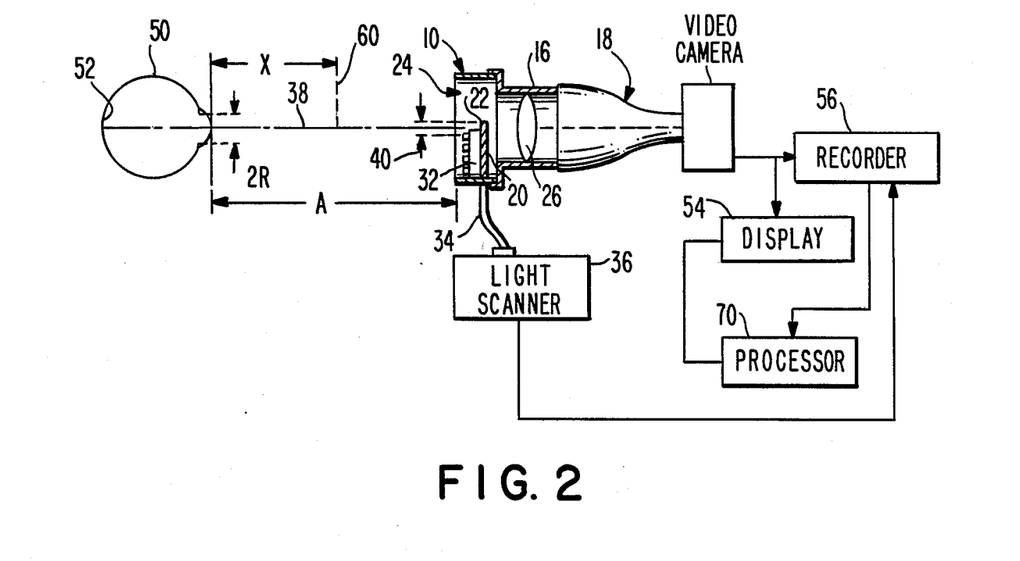
FIG. 2 is a diagrammatic illustration of the recording and evaluation system used with the photoretinoscope of FIG. 1.

As pointed out in an article entitled "Optics Of Photoretinoscope: Results From Ray Tracing", American Journal of Optometry and Physiological Optics, Volume 62, No. 9, September 1985, pp 621-625, the appearance of the crescent of light produced by a fundal reflex in the pupil of a subject's eye is a function of the camera-to-subject distance A, the pupil diameter R, the eccentricity E of the light source from the edge of the camera aperture, and the degree of defocus of the subject eye. This relationship can be expressed as follows:

$$X \leq (2R \cdot A)/(2R+E) \tag{1}$$

where X is the distance from the subject to the plane of the focus of the eye. This latter distance is illustrated in FIG. 2, where line 60 represents the plane of focus of the eye 50.

Figure 3:
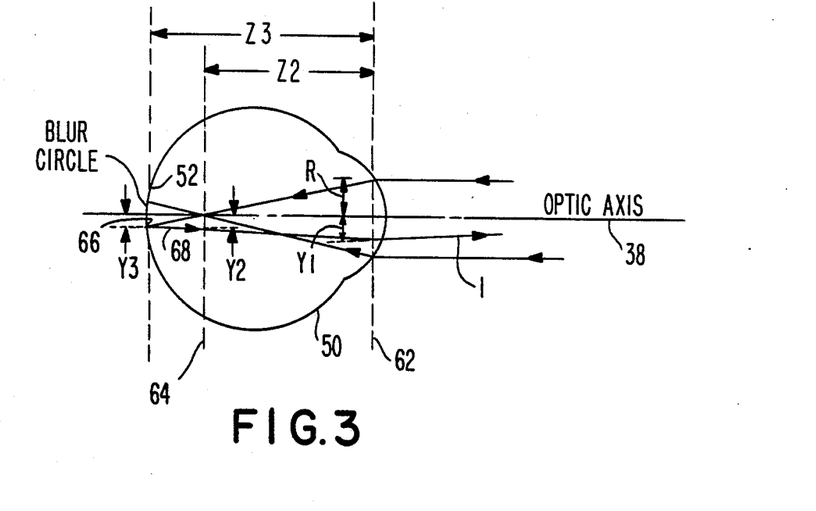
FIG. 3 is a ray trace of photorefractive images and retinal blur in a model eye.

The foregoing relationship may be visualized from the simple eye model illustrated in FIG. 3, wherein the principle plane of the eye is illustrated at 62, this line representing both the first and second principle planes. The defocus D of the eye with respect to the camera is defined as the difference between the reciprocal of the camera-to-subject distance (that is, 1/A) and the reciprocal of the distance from the eye 50 to the plane of focus 60 (that is, I/X). Thus, $D = 1/A - 1/A$. The pupil radius is illustrated in FIG. 2 with 2R being the diameter.

The ray model illustrated in FIG. 3 is a model of a myopic eye, in which the crescent due to an eccentric light source appears in the bottom of the pupil in the arrangement illustrated in FIG. 2. It will be noted that identical results are obtained for a hyperopic eye, but with the crescent appearing in the top of the pupil. As illustrated in FIG. 3, the uppermost ray of the crescent in the subject's pupil may be identified from an inspection of the optics as follows. The image of the photoretinoscope assembly 10, and specifically the image of the illuminated light source, will be focused at image plane 64, which is in front of the subject's retina 52 in the case of a myopic eye. This image appears at a distance Z2 behind the principle plane 62 of the eye, and produces at the retina an unfocused image, or blur circle, 66. If F is defined as the focal length of the eye, then the following terms can be defined:

$$F' = 1/F; \quad A' = 1/A \tag{2}$$

from this it follows that:

$$Z2 = 1/(F' - A') \tag{3}$$

The eccentricity E, which is the distance between the point source of light and the edge 22 of the camera aperture, appears in the image at plane 64 as the distance Y2, which may be defined as follows:

$$Y2 = -E \cdot Z2/A, \tag{4}$$

the negative sign being used to designate points below the optic axis 38. The distance from the second principle plane 62 to the retina is the distance Z3 where, by definition:

$$Z3 = 1/(F' + A' + D) \tag{5}$$

The radius of the blur circle 66 at the retina which is made by the point source of light, by similar traingles, is defined as follows:

$$Y3 = -(Z3 - Z2) \cdot R/Z2 \tag{6}$$

Again, the negative sign denotes the fact that the highest reflex ray in the pupil will originate from the margin of the blue circle that lies below the optic axis.

The highest ray in the pupil that will just be captured by the camera will be the ray 68 which originates from the bottom of the blur circle on the retina and just grazes the image of the aperture. This ray has a height of Y3 at the retina and Y2 at the image plane 64. Its height Y1 at the second principle plane of the eye may be computed to be:

$$Y1 = \frac{(Y2 \cdot Z3 - Y3 \cdot Z2)}{(Z3 - Z2)} \tag{7}$$

The fraction of the pupil which is dark (DF) is related to the height Y1 by the equation:

$$DF = Abs(R - Y1)/(2 \cdot R) \tag{8}$$

The foregoing set of equations was solved for Y1 and the solution was obtained as follows:

$$Y1 = R - E(A \cdot D) \tag{9}$$

which, using equation 8, means that the dark fraction is as follows:

$$DF = (E)/2 \cdot R \cdot A \cdot D \qquad (10)$$

In equation 10 the sign of D is ignored.

In the foregoing consideration, it was assumed that the first and second principle planes of the eye and the pupil area plane were all coincident, which is approximately true in the human eye. This can be done since these planes are so close together than a camera located more than a meter away and focused on any one of them would be focused on all of them. Further, the foregoing analysis is based on the projection of rays which graze the pupil area margins, and since these rays originate from more than a meter distant, the projection very closely approximates the true pupil area diameter.

In a hyperopic eye, the image of the light source and shield (i.e., the image plane 64) will lie behind the retina and the quantity Z2 will exceed Z3. In that case, the lowest rays in the pupil will originate from the lower margin of the retinal blur circle and the equations are still valid. The measurement of the drak fraction (DF) using equation 10 allows an accurate estimate of the relative defocus of the eye, using for the eccentricity the distance between the edge 22 of the aperture and the light source which produces the smallest crescent in the pupil. As previously noted, the more myopic (or hyperopic) the eye, the larger will be the blur circle. This will result in a larger image at Y1 so that a greater eccentricity is required in order to obtain the crescent effect. The linearity of the relation between defocus and eccentricity of the light source has been tested. It has been found that this relation is linear over a range of at least +6 diopters to −6 diopters as is illustrated in FIG. 4.

As illustrated by equation 10, the sensitivity to a small amount of defocus increases with the distance A between the camera and the subject. However, the light sources project a relatively narrow beam, and must be carefully aimed at the subject so that the camera will receive an adequate reflex intensity. A useful distance for testing human eyes has been found to be about one meter. In such a case, the threshold of the appearance of the first crescent is 0.5 diopters for a 5 mm diameter pupil. If the subject shows very small refractive error, a further evaluation can be made by inserting lenses of known dioptic power before the subject's eyes.

Estimation of the dark fraction (DF) can be done on the video screen 54 or by means of a suitable image processing program carried out in processor 70, which may be an IBM PC computer. The pupil radius can be easily measured on the video screen after determination of the magnification factor of the display 54.

Figure 4:
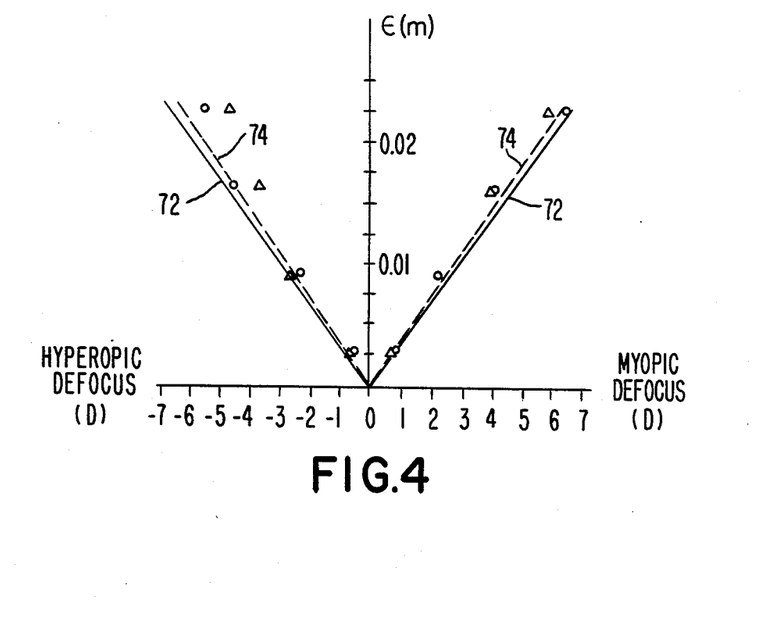
FIG. 4 is a chart showing the defocus of two artificial eyes determined by the device of FIG. 1, and measured.

The chart illustrated in FIG. 4 compares the defocus values obtained through use of the infrared photoretinoscope of the present invention as compared with measured values in two artificial eye models. As shown, the values obtained using the present invention closely match the measured values, illustrating that the present invention is capable of measuring defocus with very small refractive error in an objective manner, without the assistance of the subject. In the chart, the circles and the triangles represent measurements obtained with two different artificial eyes, the solid lines 72 represent the measured values and the dotted lines 74 represent the average error of the infrared photoretinoscope for different eccentricities of the light source.

Figure 5:
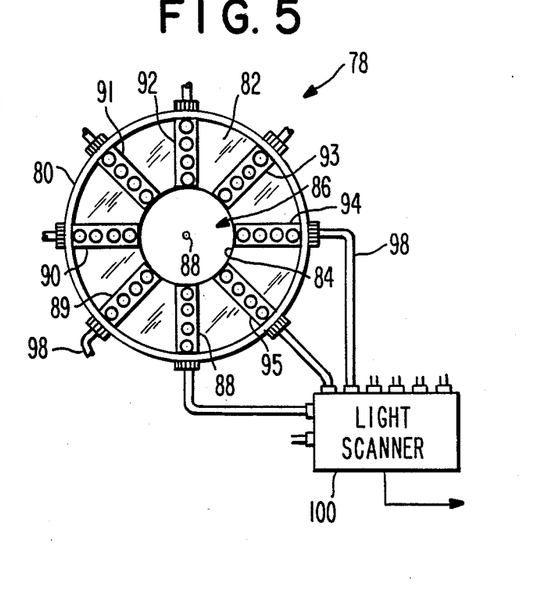
FIG. 5 is a front view of a second embodiment of the present invention.

The photoretinoscope device of FIG. 1 is illustrated with a single line of light sources, and is suitable for use in rapid screening of subjects to determine degrees of myopia and hyperopia. However, it is usually desirable to make such measurements along several meridians of the eye in order to detect variations of the eye along different radii and thus to locate and measure astigmatism in the eye. This can be accomplished with the device of FIG. 1 by rotation of the entire unit and repeating the measurements at the new angular location of the row of light sources. A preferred apparatus for accomplishing this effect is illustrated in FIG. 5, wherein a plurality of rows of light sources are arranged at spaced meridians around the circumference of the retinoscope. In this device a support ring 80 carries an annular shield 82 having a circular inner edge 84 defining a central aperture 86. The edge 84 corresponds to the edge 22 of the device of FIG. 1, while the central aperture 86 corresponds to the aperture 24 in FIG. 1. Aligned with the axis 88 of the ring 80 are a plurality of radially aligned light source housings 88-95. These housings are mounted on the right or on the shield 82, and each carries a plurality of point light sources such as the light sources 28-31 of FIG. 1. These light sources may be individual LED devices connected to a suitable scanning source, or may be the ends of corresponding fiber optic light guides which receive light from corresponding sources.

Preferably, the housings are arranged in pairs along diametrically opposed radii of the photoretinoscope 78, with the light sources being aligned their respective radii. The eccentricity of each light source is measured from the circular edge 84, and each light source cooperates with the shield edge in the manner described above with respect to the device of FIG. 1. The light scanner 100 operates to illuminate sequentially each light source in a given housing, such as housing 88, and then shifts to the next housing, such as housing 89, to sequentially illuminate each of its light sources. This continues around the photoretinoscope until all of the light sources have been illuminated, and then the sequence starts over a gain. The illumination is in the form of a short pulse of light from each light source at a rate of from 1-10 Hz, so that from 1 to 10 light pulses are produced each second. As with the device of FIG. 1, the photoretinoscope 78 is mounted on a camera to record the reflex image from the subject's eyes, the device being capable of measuring both eyes at the same time, and the results are displayed on a video screen 54 for immediate and visual analysis. The results are also recorded on a suitable video recorder together with data as to which light source is illuminated for each image so that a later evaluation of the recorded images will permit a more accurate determination of the optical characteristics of the eyes.

Although the device of FIG. 5 illustrates eight light housings arranged along four diameters of the photoretinoscope, it will be apparent that this number, and the angular relationship of the housings, can be varied, if desired.

Although the present invention has been described in terms of specific embodiments, it will be apparent that numerous variations and modifications can be made. For example, the shields 22 and 82 can be varied to provide different aperture sizes for the camera, thereby also providing different values of eccentricity for the various light sources. Such shields can be provided so that only a certain degree of defocus will provide an output from the camera. Thus, by providing a minimum defocus which will register for a given pupil size, the device can be used to rapid vision screening.

The present invention thus provides an eccentric, infrared light source for a photoretinoscope which allows objective examination of eyes from a distance, and which allows examination of both eyes at the same time. The use of multiple light sources allows a variation of the eccentricity during measurement to permit rapid evaluation of the eyes being examined, while the provision of variable shield sizes allows selection of the minimum sensitivity of the device. Furthermore, the device permits easy measurement of various meridians of the eye either by rotation of a single row of light sources, or by the provision of plural rows of light sources, or both.

What is claimed is:

1. Apparatus for testing an eye of a subject, comprising:
   camera means for registering an image, said camera means having an optical axis;
   a photoretinoscope housing mounted between said camera and a subject's eye, said housing including an opening generally coaxial with and surrounding said optical axis;
   opaque shield means mounted on said housing, said shield means being generally semicircular to occlude at least one-half of said circular opening and having an edge defining an aperture for said camera, said edge of said shield means defining a chord across said circular opening;
   a plurality of light sources aligned to form a linear array along a radial line passing through said optical axis, each light source being spaced at a different distance from said aperture edge, the distance between each light source and said edge defining a corresponding eccentricity of the light source with respect to said aperture edge, light from said light sources being directed toward a subject's eye;
   scanning means for periodically and sequentially activating said light sources to produce short bursts of light to illuminate a subject's eye, said camera means registering the reflex image produced by the reflex action of the subject's eye for each light source; and
   means for determining from the eccentricity of the light sources producing each said reflex image the defocus of a subject's eye.

2. The apparatus of claim 1, wherein said means for determining the defocus of a subject's eye includes means for recording the reflex image produced by a subject's eye for each light source and for recording the eccentricity of the light source producing each reflex image.

3. The apparatus of claim 1, wherein said housing comprises a ring mountable on the lens tube of a camera.

4. The apparatus of claim 1, wherein said light sources are infrared LED devices mounted with their output surfaces between said shield and a subject's eye to direct illumination toward the eye.

5. The apparatus of claim 1, wherein said light sources are fiber optic light guides mounted with their output ends between said shield and a subject's eye to direct illumination toward the eye.

6. The apparatus of claim 1, wherein said housing is rotatable about said optical axis to rotate said linear array of light sources about said axis to direct light along different selected meridians of a subject's eye, eccentricities of said light sources with respect to said aperture edge, light from said light sources being directed parallel to said optical axis;
   scanning means for periodically and sequentially activating said light sources to produce short bursts of light to illuminate a subject's eye, said camera means registering the reflex image produced by the reflex action of the subject's eye for each light source; and
   means for determining from the eccentricity of the light source producing each said reflex image the defocus of a subject's eye.

7. The apparatus of claim 1, wherein said camera is a video camera.

8. Apparatus for testing an eye of a subject, comprising:
   camera means for registering an image, said camera means having an optical axis;
   a photoretinoscope housing mounted between said camera and a subject's eye, said housing surrounding said optical axis;
   opaque shield means mounted in said housing, said shield means including an edge defining an aperture for said camera;
   a plurality of light sources aligned to form a linear array along a radial line passing through said optical axis, each light source being spaced at a different distance from said aperture edge, the distance between each light source and said edge defining a corresponding eccentricity of the light source with respect to said aperture edge, light from said light sources being directed toward a subject's eye;
   scanning means for periodically and sequentially activating said light sources to produce short bursts of light to illuminate a subject's eye, said camera means registering the reflex image produced by the reflex action of the subject's eye for each light source; and
   means for displaying each said reflex image as it is produced by the subject's eye for each light source in said linear array to permit immediate evaluation of the defocus of the eye and for determining from the eccentricity of the light source producing each said reflex image the amount of defocus of the subject's eye.

9. The aperture of claim 8, further including means directing light from said light sources toward both eyes of a subject whereby a reflex image is produced by each eye for each light source, said camera means registering the reflex images of both eyes simultaneously.

10. The apparatus of claim 9, wherein said means for determining the defocus of a subject's eye includes means for concurrently displaying the reflex images of both eyes to permit evaluation of the relative defocus of the subject's eyes.

11. The apparatus of claim 9, wherein said means for determining the defocus of a subject's eye further includes means for recording the reflex images produced by each light source and recording the eccentricity of the light source producing each reflex image, and further including means for determining, from the size of the recorded reflex images and from the eccentricity of the light source producing each reflex image, the degree of defocus of a subject's eyes.

12. Apparatus for testing an eye of a subject, comprising:
   camera means for registering an image, said camera means having an optical axis;

a photoretinoscope housing mounted between said camera and a subject's eye, said housing surrounding said optical axis;

opaque shield means mounted in said housing, said shield means including an edge defining an aperture for said camera;

a plurality of light sources aligned to form a linear array along a radial line passing through said optical axis, each light source being spaced at a different distance from said aperture edge, the distance between each light source and said edge defining a corresponding eccentricity of the light source with respect to said aperture edge, light from said light sources being directed toward a subject's eye;

scanning means for periodically and sequentially activating said light sources to produce short bursts of light to illuminate a subject's eye, said camera means registering the reflex image produced by the reflex action of the subject's eye for each light source;

means for recording the reflex image produced by a subject's eye for each light source, and for recording the eccentricity of the light source producing said reflex image; and means for determining from the eccentricity of the light source producing each said reflex image the defocus of a subject's eye.

13. Apparatus for testing an eye of a subject, comprising:

camera means for registering an image, said camera means having an optical axis;

a photoretinoscope housing mounted between said camera and a subject's eye, said housing surrounding said optical axis;

opaque shield means mounted in said housing, said shield means including an edge defining an aperture for said camera;

a plurality of light sources aligned to form a linear array along a radial line passing through said optical axis, each light source being spaced at a different distance from said aperture edge, the distance between each light source and said edge defining a corresponding eccentricity of the light source with respect to said aperture edge, light from said light sources being directed toward a subject's eye;

scanning means for periodically and sequentially activating said light sources to produce short bursts of light to illuminate a subject's eye, said camera means registering the reflex image produced by the reflex action of the subject's eye for each light source; and means for recording the reflex image produced by illumination of the subject's eye by each of said light sources;

means for producing the eccentricity of the light source producing said reflex image; and means for determining the degree of defocus of the subject's eye from the sizes of the reflex images and the eccentricity of the corresponding light sources producing the images.

14. The apparatus of claim 13, wherein said light sources are infrared sources mounted to direct illumination away from said shield and toward a subject's eye.

15. The apparatus of claim 14, wherein said camera is a video camera, and wherein said housing is mountable on said camera.

16. The apparatus of claim 15, further including means connected to said video camera for concurrently displaying the reflux images produced by a subject's eye as they are registered on said camera.

17. Apparatus for testing an eye, comprising:

camera means for registering an image, said camera means having an optical axis;

a photoretinoscope housing comprising a circular ring mounted between said camera and a subject's eye, said housing being coaxial with said optical axis;

opaque shield means mounted in said housing, said shield means being generally annular to occlude the outer portion of said circular ring and including an edge defining a central aperture within said ring for said camera;

a plurality of light sources mounted in said housing, said light sources being aligned along a radial line passing through said optical axis, and being spaced at different distances from said aperture edge to define corresponding eccentricities of said light sources with respect to said aperture edge, light from said light sources being directed parallel to said optical axis;

scanning means for periodically and sequentially activating said light sources to produce short bursts of light to illuminate a subject's eye, said camera means registering the reflex image produced by the reflex action of the subject's eye for each light source; and means for determining from the eccentricity of the light source producing each said reflex image the defocus of a subject's eye.

18. The apparatus of claim 17, wherein said plurality of light sources are aligned along a plurality of radial lines passing through said optical axis and spaced around said central aperture.

19. The apparatus of claim 17, wherein said light from said sources in directed to illuminate both eyes of a subject to produce two corresponding reflux images for each light source, for registration by said camera means, said means for determining the defocus of a subject's eye determining the defocus of both eyes of the subject.

20. Apparatus for testing a subject's eye, comprising:

optical means for registering an image, said optical means having an optical axis;

a housing surrounding said optical axis and located between said optical means and an eye to be tested;

opaque shield means mounted in said housing, said shield means being rotatable about said optical axis and including an edge defining a boundary of an open aperture for said optical means;

a plurality of light sources mounted on said opaque shield means, said light sources being aligned along at least one radial line passing through said optical axis, the light sources along a radial line being spaced at different distances from said aperture edge to define corresponding eccentricities with respect to said aperture edge;

means for directing light from said light sources toward a subject's eye, said shield means being rotatable about said optical axis to align said radial line of light sources with a selected meridian of the subject's eye;

means for periodically and sequentially activating said light sources to produce short bursts of light to illuminate a subject's eye and thereby product a corresponding reflux image in the eye for each light source, said images being registered by said optical means; and means for determining from the eccentricity of the light sources producing corresponding reflex images the defocus of the eye being tested.

21. The apparatus of claim 20, wherein said camera is a video camera.

22. The apparatus of claim 21, wherein said means for determining the defocus of the eye being tested includes recorder means connected to said camera for recording reflex images and for recording which light source produced each recorded reflex image.

23. Apparatus for testing a subject's eye, comprising:
optical means for registering an image, said optical means having an optical axis;
a housing surrounding said optical axis and located between said optical means and an eye to be tested;
opaque shield means mounted in said housing, said shield means including an edge defining a boundary of an open aperture for said optical means;
a plurality of light sources mounted on said opaque shield means, said light sources being aligned along a plurality of radial lines passing through said optical axis, the light sources along said radical line being spaced at different distances from said aperture edge to define corresponding eccentricities with respect to said aperture edge;
means directing light from said light sources toward a subject's eye;
means periodically and sequentially activating said light sources to produce short bursts of light to illuminate a subject's eye and thereby to produce a corresponding reflex image in the eye for registration by said optical means; and
means for determining from the eccentricity of the light sources producing corresponding reflex images the defocus of the eye being tested.

24. The apparatus of claim 23, wherein said shield means is annular, the edge of said shield means defining a central circular aperture concentric with said optical axis.

25. The apparatus of claim 24, wherein said means for directing the light from said light sources directs light toward both eyes of a subject to produce two reflex images for registration by said optical means, whereby the relative defocus of the two eyes are determined.

26. The apparatus of claim 23, wherein said shield means is perpendicular to said optical axis.

27. The apparatus of claim 26, wherein a multiplicity of light sources are aligned to form a linear array along each of said radial lines.

28. The apparatus of claim 23, wherein said means for determining the defocus of the eye being tested includes means for concurrently displaying said reflex image as it is produced by a subject's eye for each light source to permit immediate evaluation of the defocus of the eye.

29. The apparatus of claim 28, wherein said means for sequentially activating said light sources includes light scanner means for activating light sources along a selected radial line to permit evaluation of the defocus of the subject's eye along a corresponding meridian of the eye.

* * * * *

UNITED STATES PATENT AND TRADEMARK OFFICE
CERTIFICATE OF CORRECTION

PATENT NO. : 4,834,528

DATED : May 30, 1989

INVENTOR(S) : Howland et al

It is certified that error appears in the above-identified patent and that said Letters Patent is hereby corrected as shown below:

Column 1, line 6, "NIH-ROI-EY-02944" should be --NIH-ROI-EY-02994--.

Claim 1, column 9, line 46, "sources" should be --source--.

Claim 6, columns 9-10, the claim should have ended with the last words in column 9 (selected meridians of a subject's eye,) and should not have included the section beginning on column 10, line 1 (eccentricities of said light...) to line 12 (...defocus of a subject's eye).

Claim 13, column 11, line 55 "means for producing" should be --means for recording--.

Claim 13, column 11, line 56 "said" should be --each--.

Claim 16, column 12, line 1, "reflux" should be --reflex--.

Claim 19, column 12, line 38 "reflux" should be --reflex--.

Claim 20, column 12, line 65, "product" should be --produce--.

Claim 20, column 12, line 66, "reflux" should be --reflex--.

UNITED STATES PATENT AND TRADEMARK OFFICE
CERTIFICATE OF CORRECTION

PATENT NO. : 4,834,528

DATED : May 30, 1989

INVENTOR(S) : Howland et al

It is certified that error appears in the above-identified patent and that said Letters Patent is hereby corrected as shown below:

Claim 23, column 13, line 23, "said radical" should be --each radial--.

Signed and Sealed this

Twenty-seventh Day of March, 1990

Attest:

JEFFREY M. SAMUELS

*Attesting Officer*   *Acting Commissioner of Patents and Trademarks*